(12) United States Patent
Ohanian (10) Patent No.: US 12,193,959 B2
(45) Date of Patent: Jan. 14, 2025

(54) BACK BODY SUPPORT FOR POSTURE CORRECTION OR PAIN RELIEF

(71) Applicant: Ara Ohanian, Doraville, GA (US)

(72) Inventor: Ara Ohanian, Doraville, GA (US)

( * ) Notice: Subject to any disclaimer, the term of this patent is extended or adjusted under 35 U.S.C. 154(b) by 214 days.

(21) Appl. No.: 17/882,652

(22) Filed: Aug. 8, 2022

(65) Prior Publication Data

US 2022/0370228 A1    Nov. 24, 2022

Related U.S. Application Data

(63) Continuation-in-part of application No. 16/875,520, filed on May 15, 2020, now Pat. No. 11,419,426.

(51) Int. Cl.

| | | |
|---|---|---|
| A61F 6/02 | (2006.01) | |
| A47C 7/42 | (2006.01) | |
| A61F 5/02 | (2006.01) | |
| A61F 5/30 | (2006.01) | |
| A61F 5/37 | (2006.01) | |
| A47C 7/46 | (2006.01) | |
| A47C 20/02 | (2006.01) | |
| A61F 5/01 | (2006.01) | |
| B60N 2/66 | (2006.01) | |

(52) U.S. Cl.
CPC .............. *A61F 5/026* (2013.01); *A47C 7/425* (2013.01); *A61F 5/30* (2013.01); *A61F 5/3776* (2013.01); *A47C 7/46* (2013.01); *A47C 20/027* (2013.01); *A61F 2005/0183* (2013.01); *B60N 2/66* (2013.01); *B60N 2/663* (2015.04)

(58) Field of Classification Search
CPC .......... B60N 2/66; B60N 2/663; B60N 2/667; A47C 20/027; A47C 7/46; A47C 7/425; A61F 5/30; A61F 5/3776; A61F 5/3792; A61F 5/026
See application file for complete search history.

(56) References Cited

U.S. PATENT DOCUMENTS

| | | | | |
|---|---|---|---|---|
| 4,752,982 A | * | 6/1988 | Jones | A47C 20/027 5/657 |
| 11,419,426 B2 | * | 8/2022 | Ohanian | A47C 7/462 |

* cited by examiner

*Primary Examiner* — Syed A Islam
(74) *Attorney, Agent, or Firm* — Jose Cherson Weissbrot (57) ABSTRACT

The present disclosure provides a back body support 1000 that is provided with the related assemblies, such as a primary elongated cushion member 100, a secondary elongated cushion member 200, a headrest extension member 300, a flexible seating support member 400, a tail bone and buttocks support member 500, a rigid seat member 600, and a posture correction member 700, which may be coupled to one another to provide one or more combinations to be used by a user in one or more ways, such as while sitting or while walking, to provide support to back portion thereof, particularly, along the spine, and pelvis and buttock portion of a body of the user.

19 Claims, 10 Drawing Sheets

BACK BODY SUPPORT FOR POSTURE CORRECTION OR PAIN RELIEF

CROSS REFERENCE TO THE RELATED APPLICATION

The present application is in continuation-in-part (CIP) to the U.S. application Ser. No. 16/875,520.

FIELD OF THE DISCLOSURE

The present disclosure relates to field of a back body support, and, more particularly, to a back body support for posture correction or pain relief.

BACKGROUND OF THE DISCLOSURE

The usages of foam cushions are known. Conventional cushions come in familiar configurations adapted to the specific use objective of each such cushion. Examples of such cushions are described in U.S. Pat. Nos. 5,911,657; 8,740,303; 6,929,325; and 4,761,011. However, conventional cushions lack restriction in its usages and its suitability to be adjustable to support individual's vertebrae, spine, and pelvis regions.

It therefore would be desirable to provide a back body support that can be adjusted to provide a user with custom support of his or her vertebrae, for example, for posture correction and/or pain relief.

SUMMARY OF THE DISCLOSURE

In view of the foregoing disadvantages inherent in the prior art, the general purpose of the present disclosure is to provide a back body support for posture correction or pain relief to include all advantages of the prior art, and to overcome the drawbacks inherent in the prior art.

An object of the present disclosure is to provide a back body support for posture correction or pain relief.

Another object of the present disclosure is to provide a back body support for posture correction or pain relief that may be utilized in various combination and does not provide restriction in its usages and its suitability to be adjustable to support individual's vertebrae, spine, and pelvis regions.

In view of the above objects, in one main aspect of the present disclosure, a back body support includes a primary elongated cushion member extending along a horizontal plane.

The primary elongated cushion member has an outer layer, an inner layer and a liner layer.

The outer layer is adapted to support pelvis and side hip regions of a user. The outer layer includes a pelvis cushion support member and a pair of elongated hip support members. The pelvis cushion support member is adapted to support the pelvis region of the user. The pelvis cushion support member includes a first flexible material. Further, the pair of elongated hip support members is adapted to support the side hip regions of the user. Each elongated hip support member of the pair of elongated hip support members are coupled side by side to the pelvis cushion support member. Each of the elongated hip support member of the pair of elongated hip support members includes a second flexible material. The second flexible material of the pair of elongated hip support members is relatively softer than that of the first flexible material of the pelvis cushion support member. Further, the pair of elongated hip support members is aligned along the pelvis cushion support member at a height greater than a height of the pelvis cushion support member from the horizontal plane.

Further, the inner layer is coupled below the outer layer and extending across the pelvis cushion support member and at least partially across the pair of elongated hip support members. The inner layer comprises one or more blocks spaced from each other to support the pelvis cushion support member and the at least partially across the pair of elongated hip support members. The one or more blocks are of a third flexible material having hardness greater than that of the first and second flexible materials of the pelvis cushion support member and the pair of elongated hip support members.

Furthermore, the liner layer is coupled to a back side of the inner layer, opposite from the side of the inner layer that is having the outer layer, to support the inner layer and the outer layer thereon.

In one aspect of the present disclosure, the back body support further includes a secondary elongated cushion member vertically extending from, and rotatably and detachably coupled to the primary elongated cushion member to support a spine region of the user. The secondary elongated cushion member includes a vertical protrusion member and an elliptical-shaped profile member. The vertical protrusion member is rotatably and detachably coupled along a region of the pelvis cushion support member of the primary elongated cushion member. Further, the elliptical-shaped profile member snugly fits over the vertical protrusion member. The elliptical-shaped profile member includes at least one soft cushioning profile and at least one hard cushioning profile to be rotatably adjusted by a rotation of the vertical protrusion member along the region of the pelvis cushion support member of the primary elongated cushion member to provide support to the specific spine region depending upon a requirement of a hard support or a soft support to the specific spine region.

The elliptical-shaped profile member may include a length, and widths varying across the length. The length of the elliptical-shaped profile member is configured to vary to be accommodated across an entire length of the vertical protrusion member, or across a partial length of the vertical protrusion member extending from a top to along a middle portion of the vertical protrusion member to provide support a specific spine region. The widths of the elliptical-shaped profile member is configured to vary across the entire length thereof to provide support to the specific spine region without restricting a movement of shoulder of the user.

In one aspect of the present disclosure, the back body support further includes a headrest extension member detachably and adjustably coupled to the secondary elongated cushion member. The headrest extension member is configured to support a head of the user while the back body support is configured to the back of the user.

In one aspect of the present disclosure, the back body support further includes a flexible seating support member detachably coupled to the pelvis cushion support member of the primary elongated cushion member. The flexible seating support member includes a non-slip surface and is shaped to be accommodated on a conventional seat for supporting a buttock of the user while user is seating thereon.

In one aspect of the present disclosure, the back body support further includes a tail bone and buttocks support member detachably coupled to the flexible seating support member and to the pelvis cushion support member along an angular orientation between the flexible seating support member and to the pelvis cushion support member. The tail bone and buttocks support member may include a stepped and curved configuration lying along the angular orientation between the flexible seating support member and to the pelvis cushion support member.

In one aspect of the present disclosure, the back body support further includes a rigid seat member to receive the flexible seating support member thereon, and to be detachably coupled thereto. The rigid seat member includes a seating surface, and a back supporting surface extending from the seating surface. The flexible seating support member may be received on the seating surface, and the pair of elongated hip support members may be supported over the back supporting surface.

In one aspect of the present disclosure, the back body support further includes a posture correction member coupled to the primary elongated cushion member and the secondary elongated cushion member. The posture correction member includes a rigid frame structure, a pair of shoulder straps, a belt strap and a coupling member.

The rigid frame structure includes first and second horizontally aligned bar members in a spaced relation, and a third vertically aligned bar member coupled to and extending between and beyond first and second horizontally aligned bar members. The first horizontally aligned bar member may be adapted to be aligned along a shoulder of the user and the second horizontally aligned bar member is adapted to be aligned the pelvis of the user. In one example arrangement, the first horizontally aligned bar member is longer than the second horizontally aligned bar member. Further, each shoulder strap of the pair of shoulder straps is coupled to opposite distal ends of the first horizontally aligned bar member such that both the ends of each shoulder strap are met at the respective opposite distal ends. Furthermore, the belt strap is coupled to the second horizontally aligned bar member. The belt strap includes buckles to be coupled and decoupled for closing and opening. Moreover, the coupling member that may include a Velcro strip or hook and loop arrangement strip to be coupled to the third vertically aligned bar member of the rigid frame structure and across the belt strap to couple with the primary elongated cushion member and the secondary elongated cushion member, thereby coupling the primary elongated cushion member and the secondary elongated cushion member with the posture correction member.

In one main aspect of the present disclosure, a back body support includes a primary elongated cushion member extending along a horizontal plane. The back body support further includes a secondary elongated cushion member vertically extending from, and rotatably and detachably coupled to the primary elongated cushion member to support a spine region of the user. The primary elongated cushion member has an outer layer, an inner layer and a liner layer. The outer layer is adapted to support pelvis and side hip regions of a user. The outer layer includes a pelvis cushion support member and a pair of elongated hip support members. The pelvis cushion support member is adapted to support the pelvis region of the user. The pelvis cushion support member includes a first flexible material. Further, the pair of elongated hip support members is adapted to support the side hip regions of the user. Each elongated hip support member of the pair of elongated hip support members are coupled side by side to the pelvis cushion support member. Each of the elongated hip support member of the pair of elongated hip support members includes a second flexible material. The second flexible material of the pair of elongated hip support members is relatively softer than that of the first flexible material of the pelvis cushion support member. Further, the pair of elongated hip support members is aligned along the pelvis cushion support member at a height greater than a height of the pelvis cushion support member from the horizontal plane. Further, the inner layer is coupled below the outer layer and extending across the pelvis cushion support member and at least partially across the pair of elongated hip support members. The inner layer comprises one or more blocks spaced from each other to support the pelvis cushion support member and the at least partially across the pair of elongated hip support members. The one or more blocks are of a third flexible material having hardness greater than that of the first and second flexible materials of the pelvis cushion support member and the pair of elongated hip support members. Furthermore, the liner layer is coupled to a back side of the inner layer, opposite from the side of the inner layer that is having the outer layer, to support the inner layer and the outer layer thereon.

The secondary elongated cushion member includes a vertical protrusion member and an elliptical-shaped profile member. The vertical protrusion member is rotatably and detachably coupled along a region of the pelvis cushion support member of the primary elongated cushion member. Further, the elliptical-shaped profile member snugly fits over the vertical protrusion member. The elliptical-shaped profile member includes at least one soft cushioning profile and at least one hard cushioning profile to be rotatably adjusted by a rotation of the vertical protrusion member along the region of the pelvis cushion support member of the primary elongated cushion member to provide support to the specific spine region depending upon a requirement of a hard support or a soft support to the specific spine region. The elliptical-shaped profile member may include a length, and widths varying across the length. The length of the elliptical-shaped profile member is configured to vary to be accommodated across an entire length of the vertical protrusion member, or across a partial length of the vertical protrusion member extending from a top to along a middle portion of the vertical protrusion member to provide support a specific spine region. The widths of the elliptical-shaped profile member is configured to vary across the entire length thereof to provide support to the specific spine region without restricting a movement of shoulder of the user.

In one yet another main aspect of the present disclosure, a posture correction device includes a back body support and a posture correction member. The back body support includes a primary elongated cushion member, and a secondary elongated cushion member. Further, the posture correction member includes a rigid frame structure, a pair of shoulder straps, a belt strap and a coupling member. The rigid frame structure includes first and second horizontally aligned bar members in a spaced relation, and a third vertically aligned bar member coupled to and extending between and beyond first and second horizontally aligned bar members. The first horizontally aligned bar member may be adapted to be aligned along a shoulder of the user and the second horizontally aligned bar member is adapted to be aligned the pelvis of the user. In one example arrangement, the first horizontally aligned bar member is longer than the second horizontally aligned bar member. Further, each shoulder strap of the pair of shoulder straps is coupled to opposite distal ends of the first horizontally aligned bar member such that both the ends of each shoulder strap are met at the respective opposite distal ends. Furthermore, the belt strap is coupled to the second horizontally aligned bar member. The belt strap includes buckles to be coupled and decoupled for closing and opening. Moreover, the coupling member that may include a Velcro strip or hook and look arrangement strip to be coupled to the third vertically aligned bar member of the rigid frame structure and across the belt strap to couple with the primary elongated cushion member and the secondary elongated cushion member, thereby coupling the primary elongated cushion member and the secondary elongated cushion member with the posture correction member.

This together with the other aspects of the present disclosure, along with the various features of novelty that characterize the present disclosure, is pointed out with particularity in the claims annexed hereto and forms a part of the present disclosure. For a better understanding of the present disclosure, its operating advantages, and the specified object attained by its uses, reference should be made to the accompanying drawings and descriptive matter in which there are illustrated exemplary embodiments of the present disclosure.

BRIEF DESCRIPTION OF THE DRAWINGS

The advantages and features of the present disclosure will become better understood with reference to the following detailed description taken in conjunction with the accompanying drawing, in which.

Like reference numerals refer to like parts throughout the description of several views of the drawing.

DESCRIPTION OF THE DISCLOSURE

The exemplary embodiments described herein detail for illustrative purposes are subject to many variations in implementation. The present disclosure provides a back body support that include related assemblies that can be utilized in various combinations to be used by a user in one or more ways to provide support to back portion thereof, particularly, along the spine, and pelvis and buttock portion of a body of the user. It should be emphasized, however, that the present disclosure is not limited to a mantel assembly as disclosed and that it is understood that various omissions and substitutions of equivalents are contemplated as circumstances may suggest or render expedient, but these are intended to cover the application or implementation without departing from the spirit or scope of the present disclosure.

The terms "a" and "an" herein do not denote a limitation of quantity, but rather denote the presence of at least one of the referenced items.

The terms "having", "comprising", "including", and variations thereof signify the presence of a component.

The present disclosure provides a back body support 1000 that is provided with and include related assemblies, such as a primary elongated cushion member 100, a secondary elongated cushion member 200, a headrest extension member 300, a flexible seating support member 400, a tail bone and buttocks support member 500, a rigid seat member 600, and a posture correction member 700, which may be coupled to one another to provide one or more combinations to be used by a user in one or more ways, such as while seating or while walking, to provide support to back portion thereof, particularly, along the spine, and pelvis and buttock portion of a body of the user.

Figure 2A:
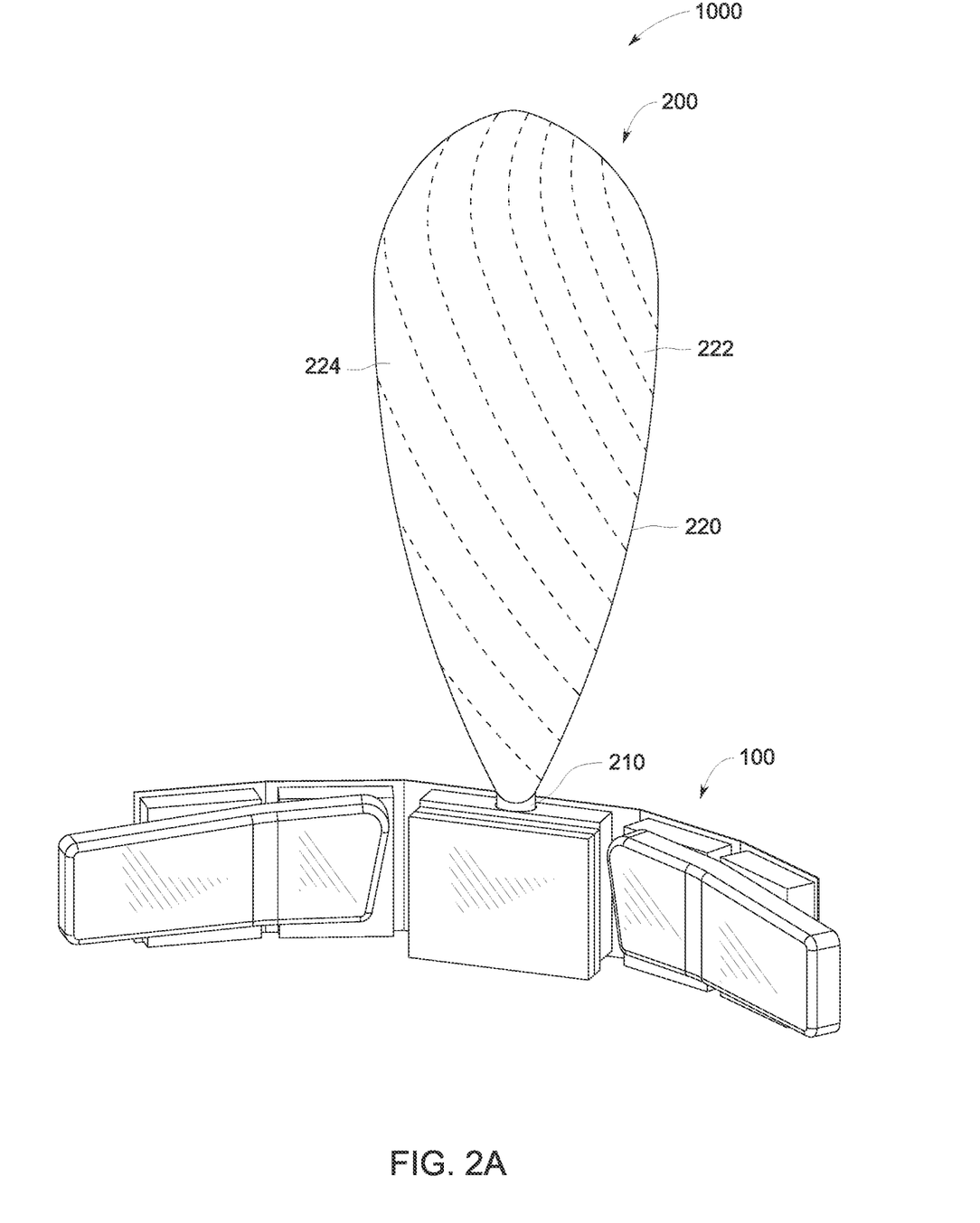
FIG. 2A illustrates a perspective view of a primary elongated cushion member and a secondary elongated cushion member of a back body support, in accordance with one exemplary embodiment of the present disclosure.
Figure 3:
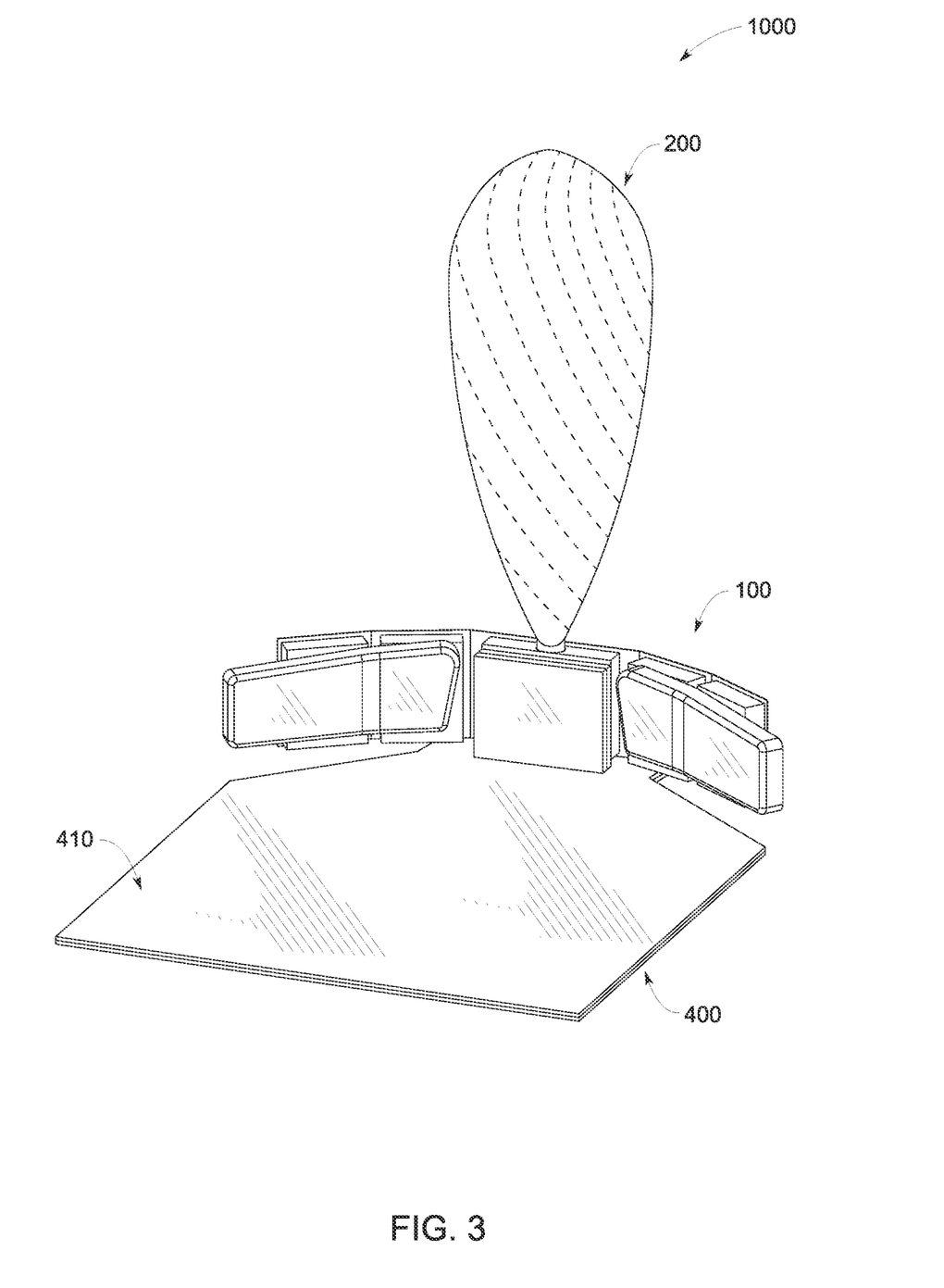
FIG. 3 illustrates a perspective view of a flexible seating support member, a primary elongated cushion member and a secondary elongated cushion member of a back body support, in accordance with one exemplary embodiment of the present disclosure.
Figure 4A:
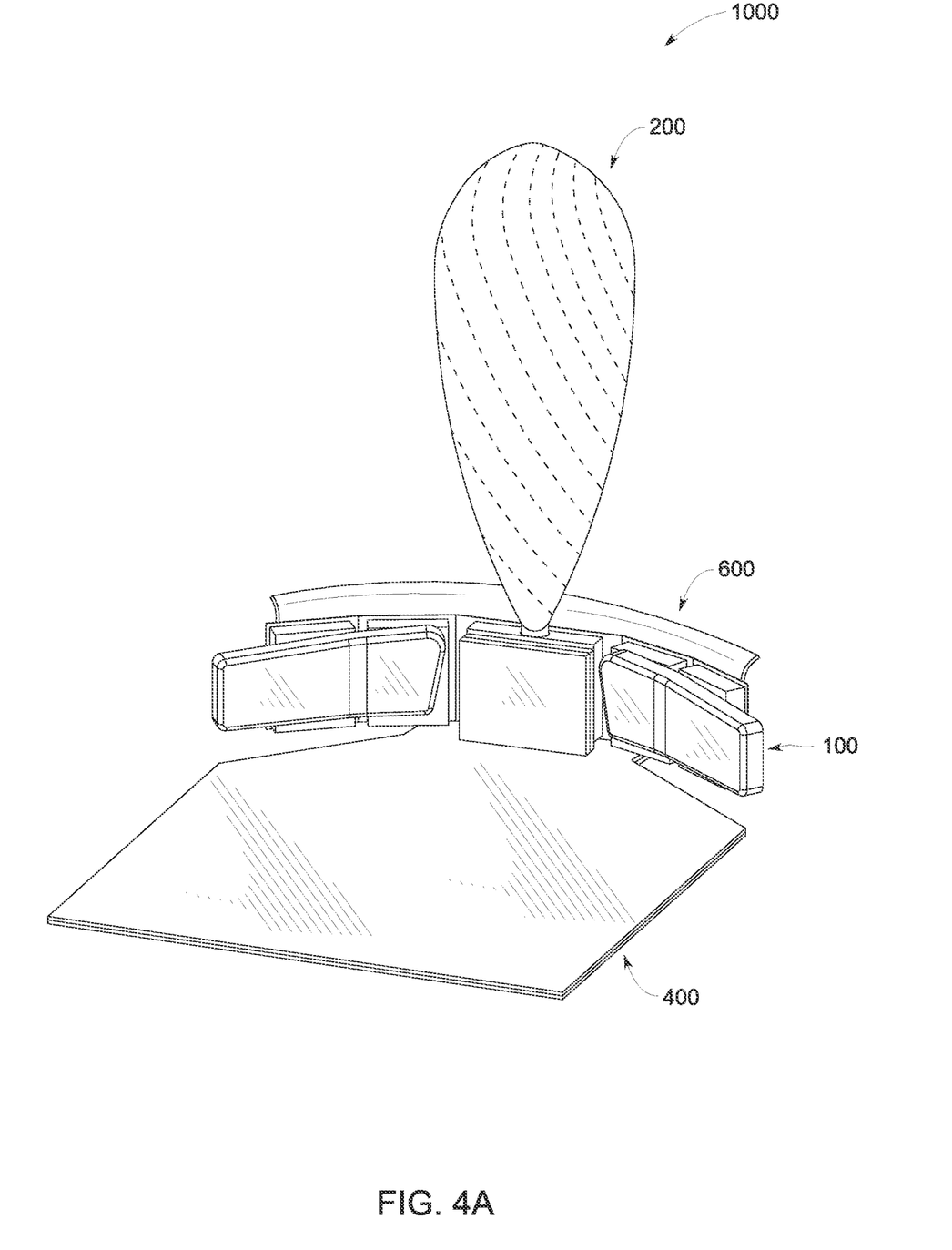
FIGS. 4A and 4B, respectively, illustrate an assembled view and an exploded view of a rigid seat member, a flexible seating support member, a primary elongated cushion member and a secondary elongated cushion member of a back body support, in accordance with one exemplary embodiment of the present disclosure.
Figure 4B:
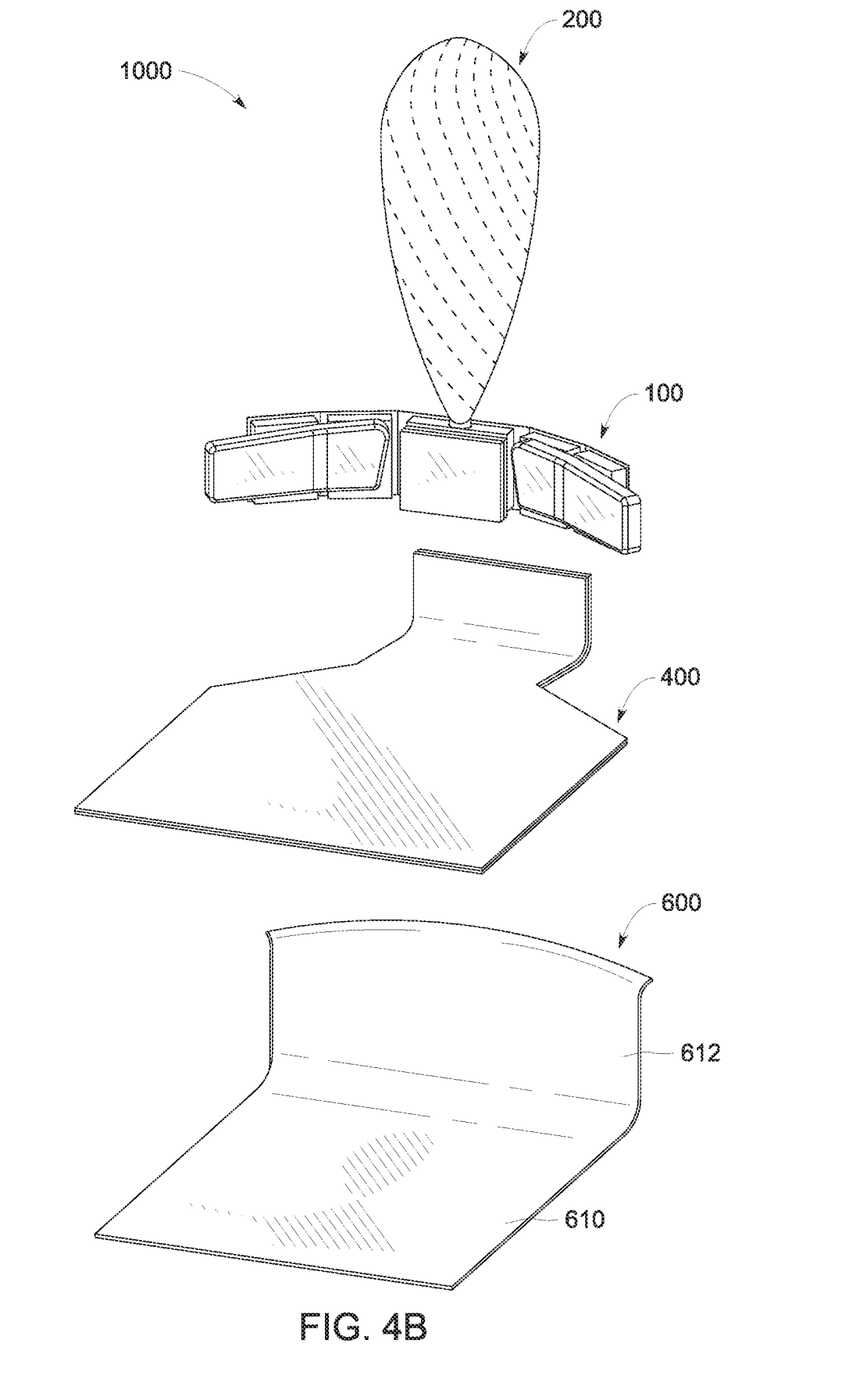
Figure 5:
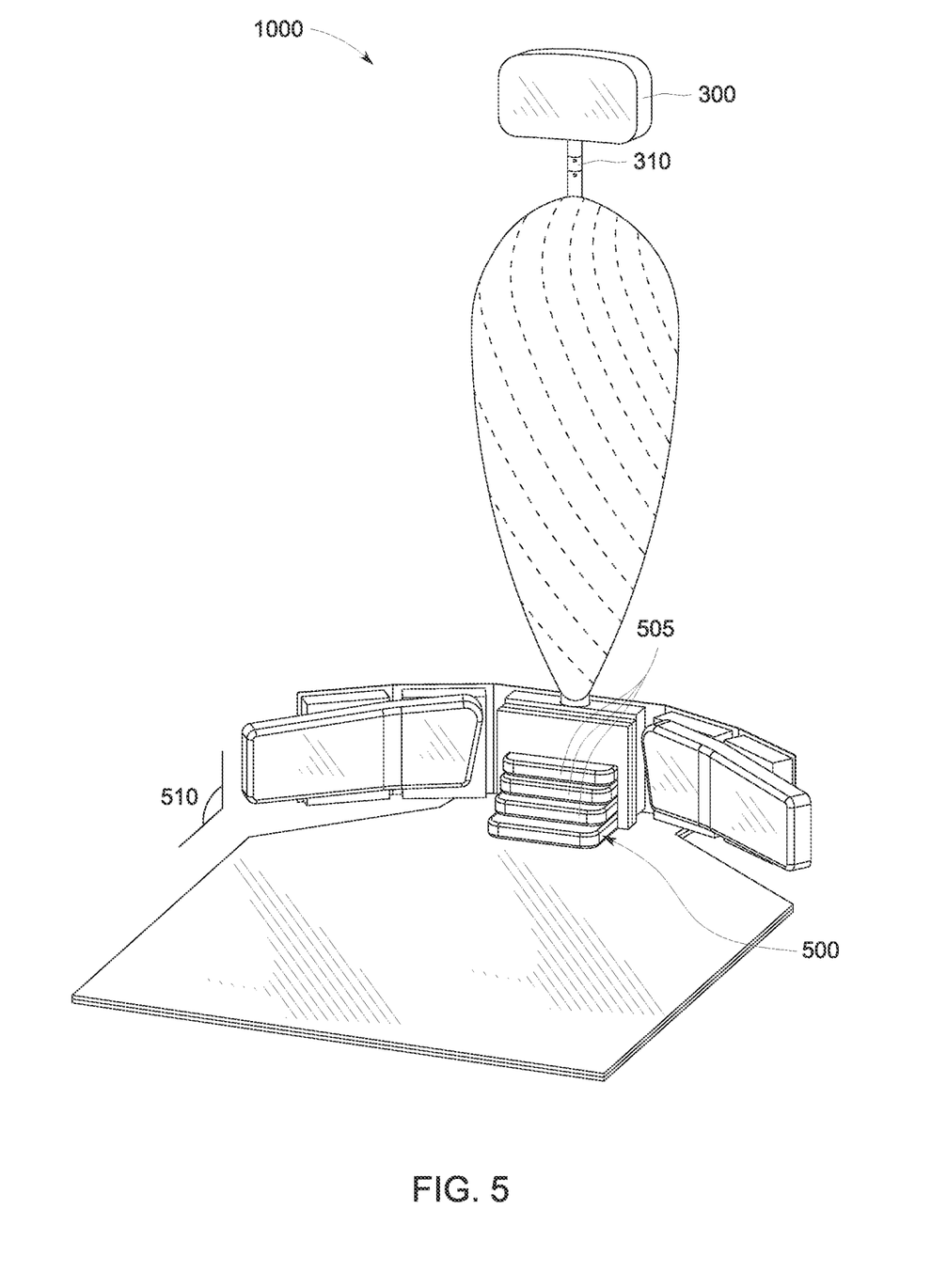
FIG. 5 illustrate a perspective view of a back body support having a headrest extension member coupled to a secondary elongated cushion member, and a tail bone and buttocks support member coupled at an angular orientation of a primary elongated cushion member and a secondary elongated cushion member, along with a rigid seat member, a flexible seating support member, in accordance with one exemplary embodiment of the present disclosure.
Figure 6A:
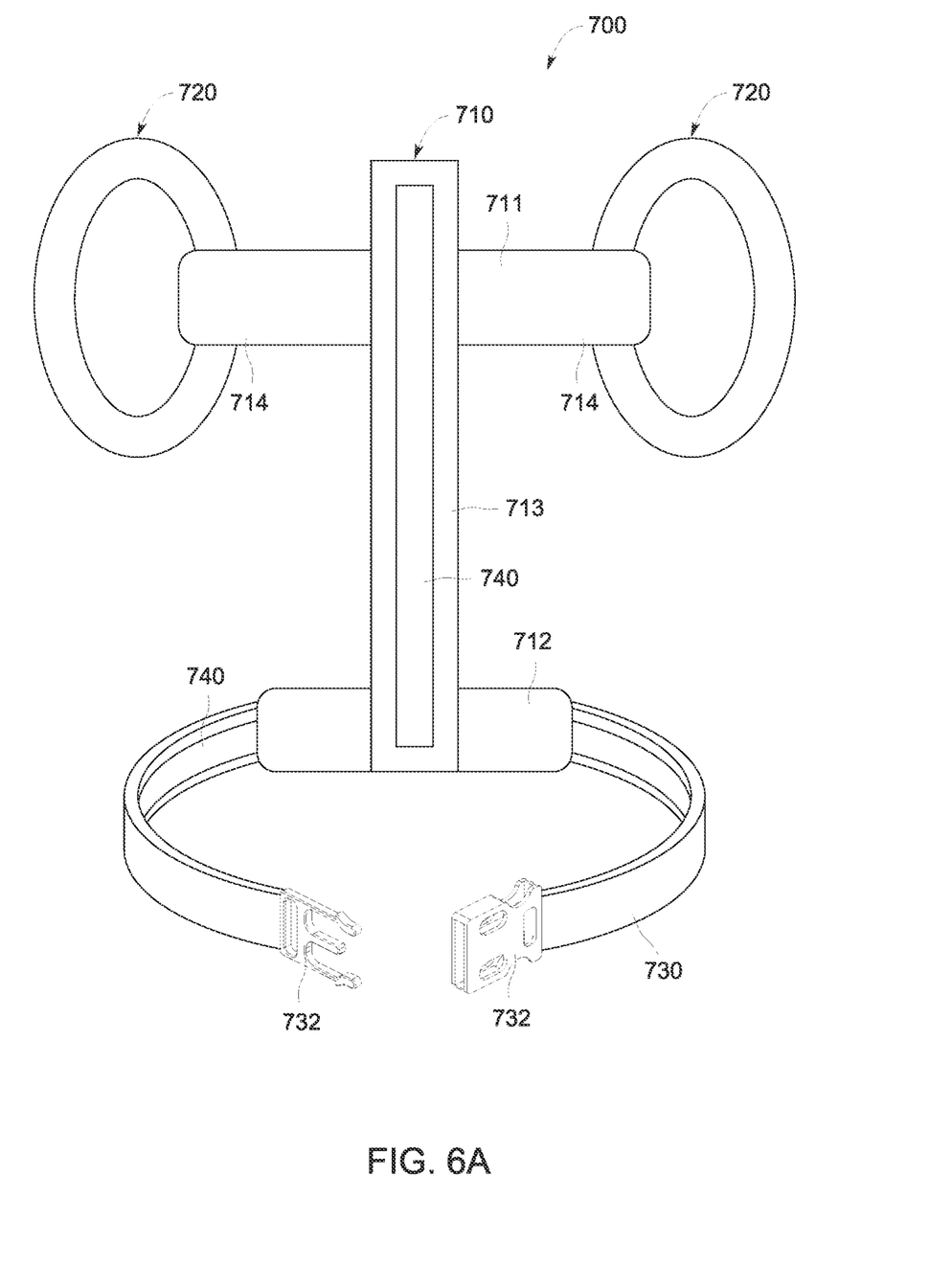
FIG. 6A illustrate a perspective view of a posture correction member to be coupled with a back body support having a primary elongated cushion member and a secondary elongated cushion member, in accordance with one exemplary embodiment of the present disclosure.
Figure 6B:
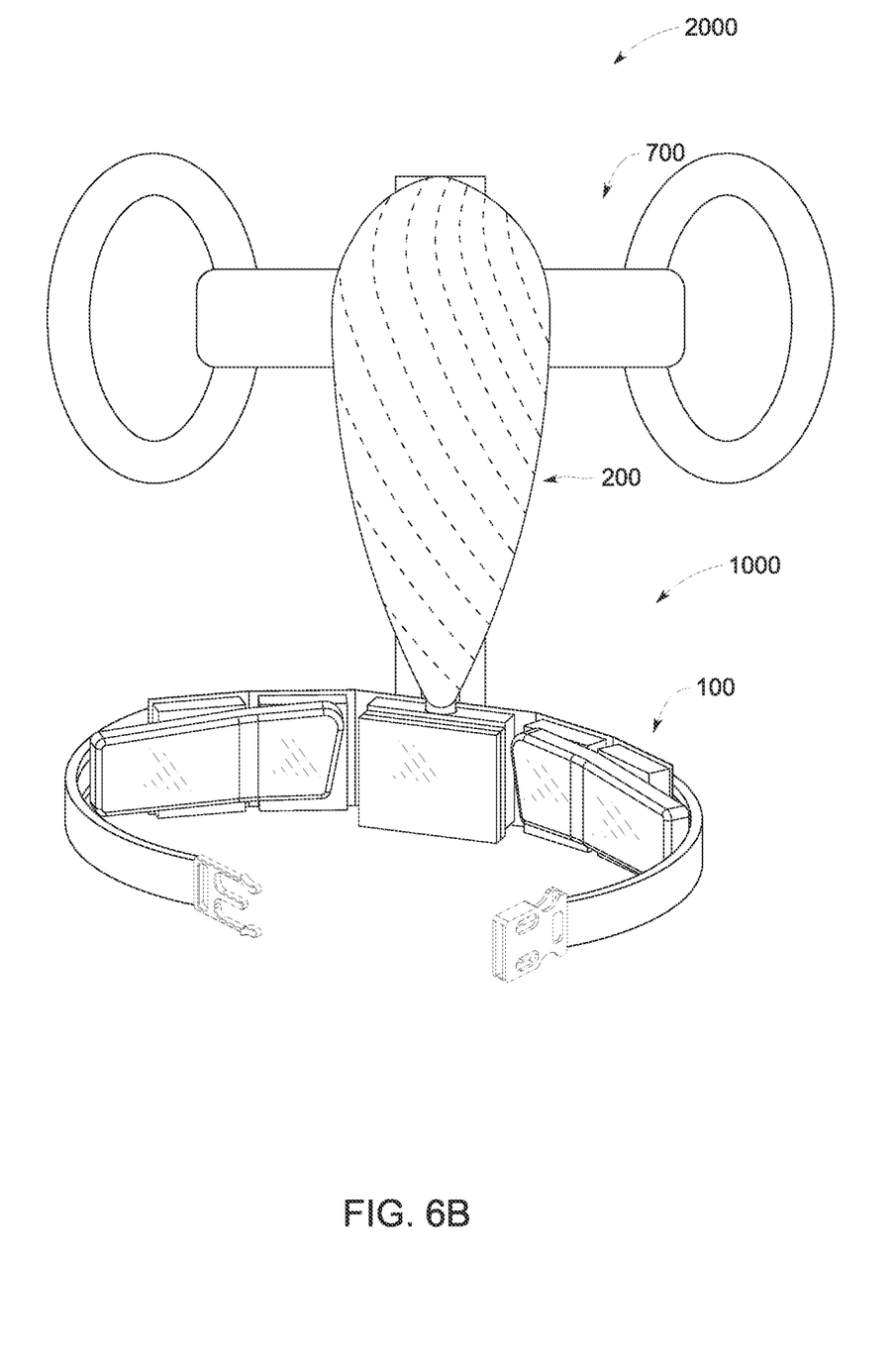
FIG. 6B illustrate a perspective view of a posture correction member coupled with a back body support having a primary elongated cushion member and a secondary elongated cushion member, in accordance with one exemplary embodiment of the present disclosure.

The back body support 1000 that is provided with the include related assemblies, such as a primary elongated cushion member 100, a secondary elongated cushion member 200, a headrest extension member 300, a flexible seating support member 400, a tail bone and buttocks support member 500, a rigid seat member 600, and a posture correction member 700 will now be described in conjunction with FIGS. 1A to 6B. In particular, FIGS. 1A and 1B, respectively, illustrate a perspective view and a top view of a primary elongated cushion member of a back body support; FIG. 2A illustrates a perspective view of a primary elongated cushion member and a secondary elongated cushion member of a back body support; FIG. 2A illustrates a perspective view of a primary elongated cushion member and a secondary elongated cushion member of a back body support; FIG. 3 illustrates a perspective view of a flexible seating support member, a primary elongated cushion member and a secondary elongated cushion member of a back body support; FIGS. 4A and 4B, respectively, illustrate an assembled view and an exploded view of a rigid seat member, a flexible seating support member, a primary elongated cushion member and a secondary elongated cushion member of a back body support; FIG. 5 illustrate a perspective view of a back body support having a headrest extension member coupled to a secondary elongated cushion member, and a tail bone and buttocks support member coupled at an angular orientation of a primary elongated cushion member and a secondary elongated cushion member, along with a rigid seat member, a flexible seating support member; FIG. 6A illustrate a perspective view of a posture correction member to be coupled with a back body support having a primary elongated cushion member and a secondary elongated cushion member; and FIG. 6B illustrate a perspective view of a posture correction member coupled with a back body support having a primary elongated cushion member and a secondary elongated cushion member, in accordance with various exemplary embodiments of the present disclosure.

Figure 1A:
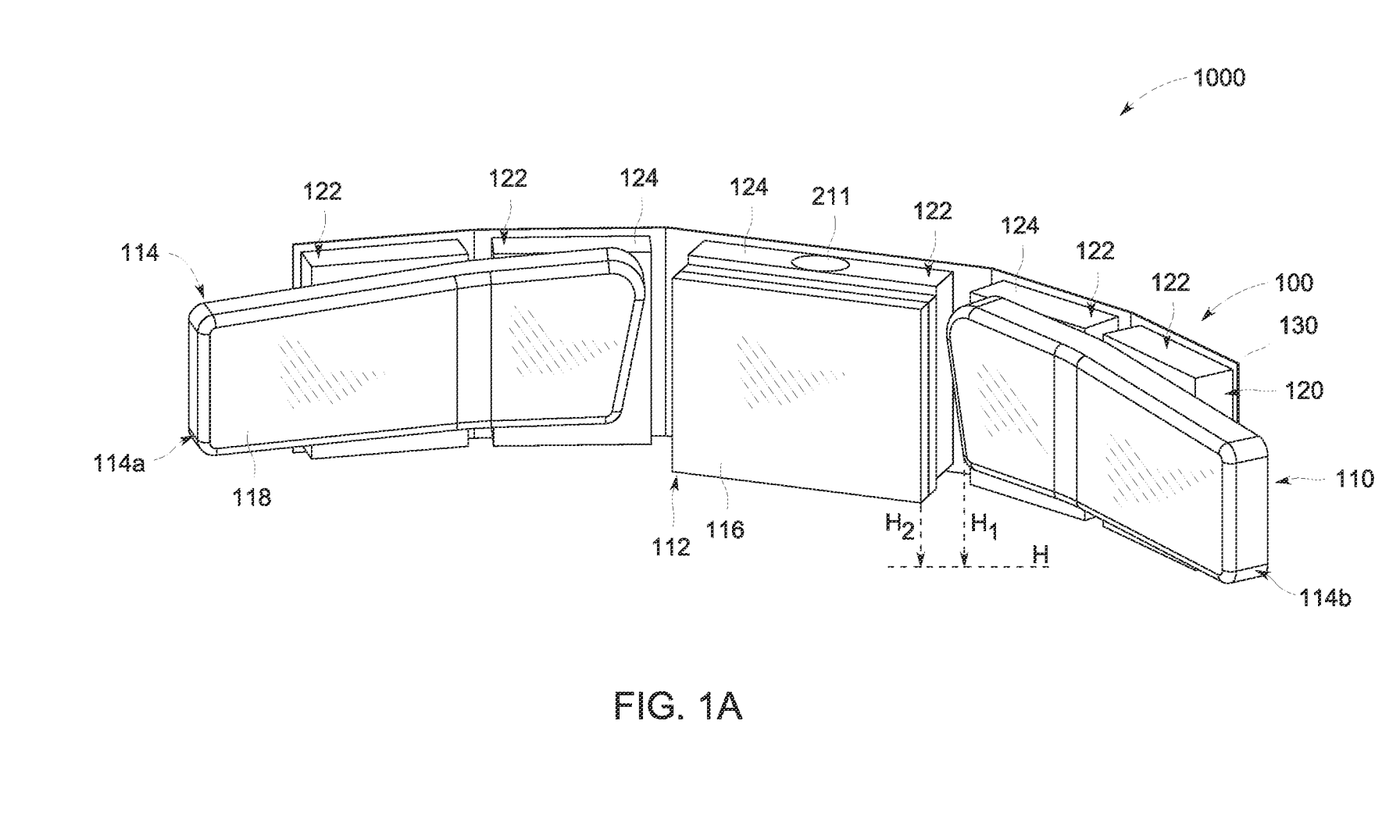
FIGS. 1A and 1B, respectively, illustrate a perspective view and a top view of a primary elongated cushion member of a back body support, in accordance with an exemplary embodiment of the present disclosure.
Figure 1B:
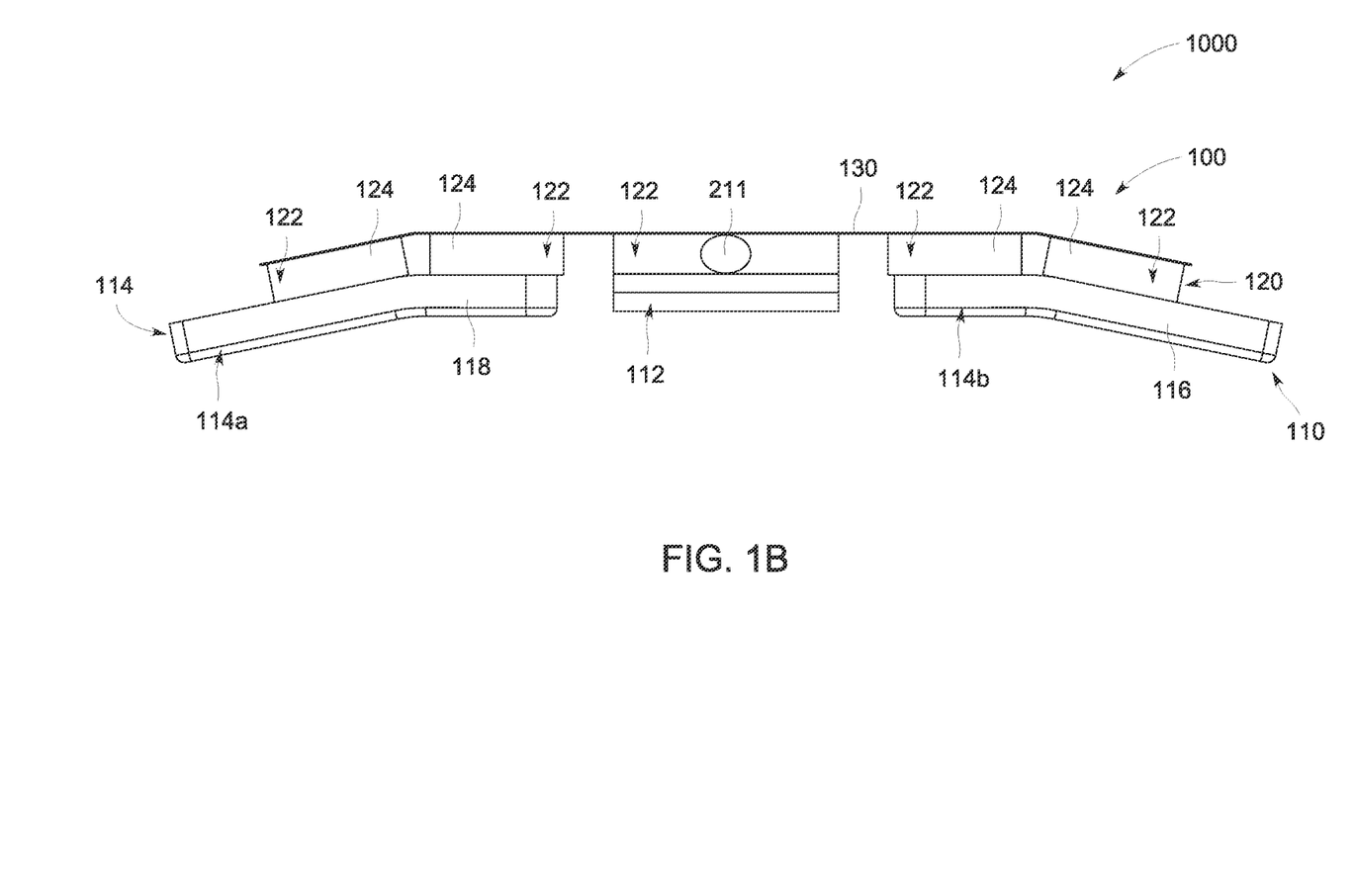

Referring now to FIGS. 1A and 1B, in one main aspect of the present disclosure, the back body support 1000 includes a primary elongated cushion member 100 extending along a horizontal plane (H). The primary elongated cushion member 100 may be adapted to be used by the user along a pelvis region of the body while the user is sitting or walking. When the user is walking, the primary elongated cushion member 100 may include strap to secure the primary elongated cushion member 100 along the pelvis region of the user.

The primary elongated cushion member 100 may include an outer layer 110, an inner layer 120 and a liner layer 130.

The outer layer 110 is adapted to support the pelvis and side hip regions of the user. The outer layer 100 includes a pelvis cushion support member 112 and a pair of elongated hip support members 114. The pelvis cushion support member 112 is adapted to support the pelvis region of the user. The pelvis cushion support member 112 includes a first flexible material 116. Further, the pair of elongated hip support members 114 is adapted to support the side hip regions of the user. Each elongated hip support member 114a, 114b of the pair of elongated hip support members 114 are coupled side by side to the pelvis cushion support member 112. Each of the elongated hip support member 114a, 114b of the pair of elongated hip support members 114 includes a second flexible material 118. The second flexible material 118 of the pair of elongated hip support members 114 is relatively softer than that of the first flexible material 116 of the pelvis cushion support member 112. Further, the pair of elongated hip support members 114 is aligned along the pelvis cushion support member 112 at a height (H1) greater than a height (H2) of the pelvis cushion support member 112 from the horizontal plane (H). Such lower height (H2) of the pelvis cushion support member 112 from the horizontal ground (H) may enable proper positioning of the primary elongated cushion member 100 on seats while the pair of elongated hip support members 114 remain in raised position to properly support the hip portion of the user. Further, such height (H2) may also enable coupling of the pelvis cushion support member 112 with the flexible seating support member 400, while the pair of elongated hip support members 114 remain untouched and coupled with the flexible seating support member 400, as seen in FIG. 3.

Further, as seen in FIGS. 1A and 1B, the inner layer 120 is coupled below the outer layer 110 and extending across the pelvis cushion support member 112 and at least partially across the pair of elongated hip support members 114. The inner layer 120 may include one or more blocks 122 spaced from each other to support the pelvis cushion support member 112 and the at least partially across the pair of elongated hip support members 114. One or more blocks 122 are of a third flexible material 124 having hardness greater than that of the first and second flexible materials 116, 118 of the pelvis cushion support member 112 and the pair of elongated hip support members 114.

In one example, the first flexible material 116 may be of soft memory foam including silicone gel, or any other soft foam. The second flexible material 118 may also be of memory foam including silicone gel, or any other foam memory, relatively harder than that of the soft memory foam including silicone gel, or any other soft foam of the first flexible material 116. Further, the third flexible material 124 may be of a rigid or semi-rigid foam, spaced out for a belt-like fit along the inner layer 120.

Furthermore, the liner layer 130 is coupled to a back side of the inner layer 120, opposite from the side of the inner layer that is having the outer layer 110, to support the inner layer 120 and the outer layer 110 thereon. The liner layer 130 may be of a fabric material, which is flexible that may enable folding of the primary elongated cushion member 100.

Figure 2B:
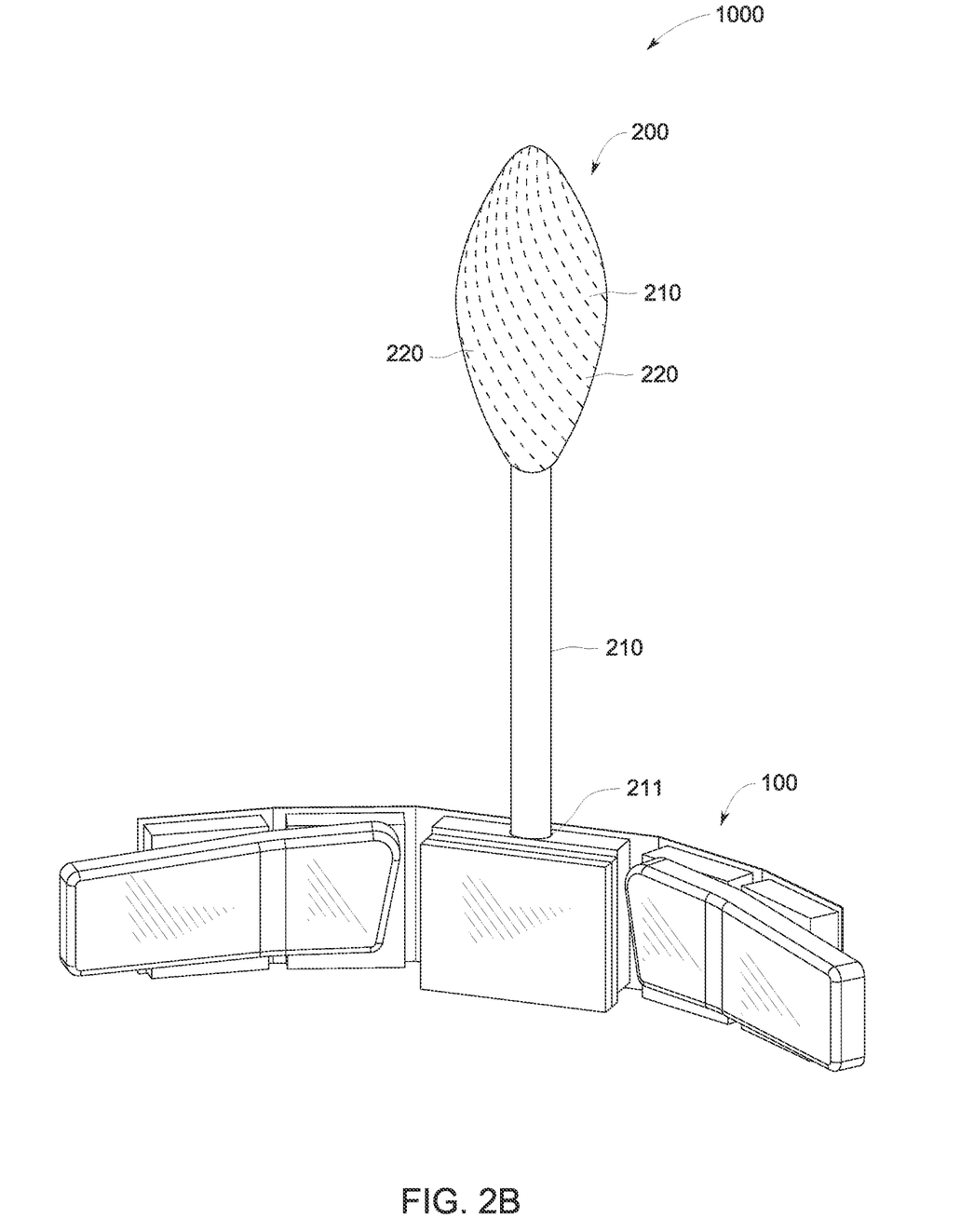
FIG. 2B illustrates a perspective view of a primary elongated cushion member and a secondary elongated cushion member of a back body support, in accordance with one exemplary embodiment of the present disclosure.

Referring now to FIGS. 2A and 2B to describe the primary elongated cushion member 100 and the secondary elongated cushion member 200 as in combination to obtain the back body support 100. FIGS. 2A and 2B illustrate perspective view of the primary elongated cushion member 100 and the secondary elongated cushion member 200 of the back body support 1000, in accordance with various embodiments of the present disclosure. In one aspect of the present disclosure, the back body support 1000 further includes a secondary elongated cushion member 200 vertically extending from, and rotatably and detachably coupled to the primary elongated cushion member 100 to support a spine region of the user. The secondary elongated cushion member 200 includes a vertical protrusion member 210 and an elliptical-shaped profile member 220. The vertical protrusion member 210 is rotatably and detachably coupled along a region of the pelvis cushion support member 112 of the primary elongated cushion member 100. As seen in FIG. 2A, the region of the pelvis cushion support member 112 include a recess 211 to snugly receive the vertical protrusion member 210 therein to rotatably and detachably couple the secondary elongated cushion member 200 with the primary elongated cushion member 100.

Further, the elliptical-shaped profile member 220 snugly fits or rigidly fixed over the vertical protrusion member 210. The elliptical-shaped profile member 220 includes at least one soft cushioning profile 222 and at least one hard cushioning profile 224 to be rotatably adjusted by a rotation of the vertical protrusion member 210 along the region of the pelvis cushion support member 112 of the primary elongated cushion member 100 to provide support to the specific spine region depending upon a requirement of a hard support or a soft support to the specific spine region.

The elliptical-shaped profile member 220 may include a length, and widths varying across the length. The length of the elliptical-shaped profile member 220 is configured to vary to be accommodated across an entire length of the vertical protrusion member 210, as seen in FIG. 2A; or across a partial length of the vertical protrusion member 210 extending from a top to along a middle portion of the vertical protrusion member 210, as seen in FIG. 2B, to provide support a specific spine region. The widths of the elliptical-shaped profile member 220 is configured to vary across the entire length thereof to provide support to the specific spine region without restricting a movement of the user's shoulder.

In one aspect of the present disclosure, as seen in FIG. 5, the back body support 1000 further includes a headrest extension member 300 detachably and adjustably coupled to the secondary elongated cushion member 200. The headrest extension member 300 is configured to support a head of the user while the back body support 1000 is configured to the back of the user. The headrest extension member 300 may include a sliding arrangement or a telescopic arrangement 310 to enable extension and adjustments thereof.

Referring now to FIG. 3, in one aspect of the present disclosure, the back body support 1000 further includes a flexible seating support member 400 detachably coupled to the pelvis cushion support member 112 of the primary elongated cushion member 100 due to the height (H2) more closer to the horizontal plane. In one example arrangement the flexible seating support member 400 may be detachably coupled to the pelvis cushion support member 112 via a suitable coupling means such as Velcro strip or a hook and look arrangement (not shown). The flexible seating support member 400 includes a non-slip surface 410 and is shaped to be accommodated on a conventional seat for supporting a buttock of the user while user is sitting thereon.

In one aspect of the present disclosure, as seen in FIG. 5, the back body support 1000 further includes a tail bone and buttocks support member 500 detachably coupled to the flexible seating support member 400 and to the pelvis cushion support member 112 along an angular orientation 510 between the flexible seating support member 400 and to the pelvis cushion support member 112. The tail bone and buttocks support member 500 may include a stepped and curved configuration 505 lying along the angular orientation 510 between the flexible seating support member 400 and to the pelvis cushion support member 112. However, without departing from the scope of the present disclosure, the tail bone and buttocks support member 500 may be of a slopped profile defining a curvature to comfortably accommodate the pelvis of the user to provide support thereto. Detachably coupling of the tail bone and buttocks support member 500 with the flexible seating support member 400 and the pelvis cushion support member 112 along the angular orientation 510 between the flexible seating support member 400 and to the pelvis cushion support member 112 may be provided by a hook and loop strap or a Velcro strap (not shown).

The back body support 1000 including the primary elongated cushion member 100, the secondary elongated cushion member 200, the flexible seating support member 400, and optionally, the headrest extension member 300 and the tail bone and buttocks support member 500 may enable to form the back body support 1000, which may be utilized to by the user in a sitting position when sitting on a chair or an office chair.

Referring now to FIGS. 4A and 4B, in one aspect of the present disclosure. FIGS. 4A and 4B, respectively, illustrate an assembled view and an exploded view of a rigid seat member 600, the flexible seating support member 400, a primary elongated cushion member 100 and a secondary elongated cushion member 200 of a back body support 1000. As seen, the back body support 1000 further includes the rigid seat member 600 to receive the flexible seating support member 400 thereon, and to be detachably coupled thereto via a hook and loop strap or a Velcro strap (not shown). The rigid seat member 600 may include a seating surface 610, and a back supporting surface 612 extending from the seating surface 610. The flexible seating support member 400 may be received on the seating surface 610, and the pair of elongated hip support members 114 may be supported over the back supporting surface 612. The back body support 1000 having the rigid seat member 600 may be utilized for sitting thereon, or may be kept as part of the conventional seat for sitting of the user for back support and relief.

Referring now to FIGS. 6A and 6B, in one aspect of the present disclosure, the back body support 1000 further includes a posture correction member 700 coupled to the primary elongated cushion member 100 and the secondary elongated cushion member 200. The posture correction member 700 includes a rigid frame structure 710, a pair of shoulder straps 720, a belt strap 730 and a coupling member 740. As seen, FIG. 6A illustrate a perspective view of the posture correction member 700 to be coupled with the back body support 1000 having the primary elongated cushion member 100 and the secondary elongated cushion member 200; and FIG. 6B illustrate a perspective view of the posture correction member 7000 coupled with the back body support 1000 having the primary elongated cushion member 100 and the secondary elongated cushion member 200, in accordance with various exemplary embodiments of the present disclosure.

As seen in FIG. 6A, the rigid frame structure 710 may include first and second horizontally aligned bar members 711, 712 in a spaced relation, and a third vertically aligned bar member 713 coupled to and extending between and beyond first and second horizontally aligned bar members 711, 712. The first horizontally aligned bar member 711 may be adapted to be aligned along a shoulder of the user and the second horizontally aligned bar member 712 is adapted to be aligned the pelvis of the user. In one example arrangement, the first horizontally aligned bar member 711 is longer than the second horizontally aligned bar member 712. Further, each shoulder strap of the pair of shoulder straps 720 is coupled to opposite distal ends 714 of the first horizontally aligned bar member 711 such that both the ends of each shoulder strap 720 are met at the respective opposite distal ends 714. Furthermore, the belt strap 730 is coupled to the second horizontally aligned bar member 712. The belt strap 730 includes buckles 732 to be coupled and decoupled for closing and opening. Moreover, the coupling member 740 that may include a Velcro strip or hook and look arrangement strip 742 to be coupled to the third vertically aligned bar member 713 of the rigid frame structure 710 and across the belt strap 730 to couple with the primary elongated cushion member 100 and the secondary elongated cushion member 200, thereby coupling the primary elongated cushion member 100 and the secondary elongated cushion member 200 with the posture correction member 700.

The back body support 1000 with the posture correction member 700 may be utilized by the user when the user is walking. When the user is walking and want to use the back body support 1000 having the primary elongated cushion member 100 and the secondary elongated cushion member 200, the user may couple the back body support 1000 having the primary elongated cushion member 100 and the secondary elongated cushion member 200 with the posture correction member 700 via the coupling member 740 that may include the Velcro strip or hook and look arrangement strip 742. Once coupled, the user may wear the back body support 1000 with the posture correction member 700 to walk.

All the components, such as the primary elongated cushion member 100, the secondary elongated cushion member 200, the headrest extension member 300, the flexible seating support member 400, the tail bone and buttocks support member 500, the rigid seat member 600, and the posture correction member 700 of the back body support 1000 may be in a package or may be separate, and can be used by the user in various combination as per the requirement of the user, either the user is walking or sitting.

The present disclosure is advantageous in providing a back body support for posture correction or pain relief that that may be utilized in various combination and provides does no restriction in its usages and its suitability to be adjustable to support individual's vertebrae, spine, and pelvis regions.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, and to thereby enable others skilled in the art to best utilize the present disclosure and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present disclosure.

What is claimed is:

1. A back body support comprising:
    a primary elongated cushion member extending along a horizontal plane (H), the primary elongated cushion member having:
    an outer layer adapted to support pelvis and side hip regions of a user, the outer layer having,
    a pelvis cushion support member adapted to support the pelvis region of the user, wherein the pelvis cushion support member having a first flexible material, and
    a pair of elongated hip support members adapted to support the side hip regions of the user, each elongated hip support member, of the pair of elongated hip support members are coupled side by side to the pelvis cushion support member, each of the elongated hip support member, of the pair of elongated hip support members having a second flexible material,
    wherein the pair of elongated hip support members is aligned along the pelvis cushion support member at a height greater than a height of the pelvis cushion support member from the horizontal plane (H),
    an inner layer coupled below the outer layer and extending across the pelvis cushion support member and at least partially across the pair of elongated hip support members, and
    a liner layer coupled to the inner layer to support the inner layer and the outer layer; and
    a secondary elongated cushion member vertically extending from, and rotatably and detachably coupled to the primary elongated cushion member to support a spine region of the user, the secondary elongated cushion member having,
    a vertical protrusion member rotatably and detachably coupled along a region of the pelvis cushion support member of the primary elongated cushion member,
    an elliptical-shaped profile member snugly fits over the vertical protrusion member,
    the elliptical-shaped profile member having at least one soft cushioning profile and at least one hard cushioning profile to be rotatably adjusted by a rotation of the vertical protrusion member along the region of the pelvis cushion support member of the primary elongated cushion member to provide support to the specific spine region depending upon a requirement of a hard support or a soft support to the specific spine region.

2. The back body support as claimed in claim 1, wherein the second flexible material of the pair of elongated hip support members is relatively softer than that of the first flexible material of the pelvis cushion support member.

3. The back body support as claimed in claim 2, wherein, the inner layer comprises one or more blocks spaced from each other to support the pelvis cushion support member and the at least partially across the pair of elongated hip support members, wherein the one or more blocks are of a third flexible material having hardness greater than that of the first and second flexible materials, of the pelvis cushion support member and the pair of elongated hip support members.

4. The back body support as claimed in claim 1, wherein the elliptical-shaped profile member comprises a length, and widths varying across the length, wherein the length of the elliptical-shaped profile member is configured to vary to be accommodated across an entire length of the vertical protrusion member, or across a partial length of the vertical protrusion member extending from a top to along a middle portion of the vertical protrusion member to provide support a specific spine region, and wherein the widths of the elliptical-shaped profile member is configured to vary across the entire length thereof to provide support to the specific spine region without restricting a movement of shoulder of the user.

5. The back body support as claimed in claim 1 further comprising:
    a headrest extension member detachably and adjustably coupled to the secondary elongated cushion member, the headrest extension member is configured to support a head of the user while the back body support is configured to the back of the user.

6. The back body support as claimed in claim 1 further comprising:
    a flexible seating support member detachably coupled to the pelvis cushion support member of the primary elongated cushion member,
    wherein the flexible seating support member comprises a non-slip surface and is shaped to be accommodated on a conventional seat for supporting a buttock of the user while user is seating thereon.

7. The back body support as claimed in claim 6 further comprising:
    a tail bone and buttocks support member detachably coupled to the flexible seating support member and to the pelvis cushion support member along an angular orientation between the flexible seating support member and to the pelvis cushion support member,
    wherein the tail bone and buttocks support member comprises a stepped and curved configuration lying along the angular orientation between the flexible seating support member and to the pelvis cushion support member.

8. The back body support as claimed in claim 6 further comprising:
    a rigid seat member to receive the flexible seating support member thereon, and to be detachably coupled thereto, the rigid seat member having,
    a seating surface, and
    a back supporting surface extending from the seating surface,
    wherein the flexible seating support member is received on the seating surface, and the pair of elongated hip support members is supported over the back supporting surface.

9. The back body support as claimed in claim 1 further comprising:
    a posture correction member coupled to the primary elongated cushion member and the secondary elongated cushion member, the posture correction member having,
    a rigid frame structure, the rigid frame structure including,
    first and second horizontally aligned bar members, in a spaced relation, wherein the first horizontally aligned bar member is adapted to be aligned along a shoulder of the user and the second horizontally aligned bar member is adapted to be aligned the pelvis of the user, and wherein the first horizontally aligned bar member is longer than the second horizontally aligned bar member, and a third vertically aligned bar member coupled to and extending between and beyond first and second horizontally aligned bar members;

a pair of shoulder straps, each shoulder strap of the pair of shoulder straps is coupled to opposite distal ends of the first horizontally aligned bar member such that both the ends of each shoulder strap are met at the respective opposite distal ends, a belt strap coupled to the second horizontally aligned bar member, the belt strap having buckles to be coupled and decoupled for closing and opening, and a coupling member including a hook-and-loop arrangement strip coupled to the third vertically aligned bar member of the rigid frame structure and across the belt strap to couple with the primary elongated cushion member and the secondary elongated cushion member, thereby coupling the primary elongated cushion member and the secondary elongated cushion member with the posture correction member.

10. A back body support comprising:
a primary elongated cushion member extending along a horizontal plane (H), the primary elongated cushion member having:
an outer layer adapted to support pelvis and side hip regions of a user, the outer layer having,
a pelvis cushion support member adapted to support the pelvis region of the user, wherein the pelvis cushion support member having a first flexible material; and
a pair of elongated hip support members adapted to support the side hip regions of the user, each elongated hip support member, of the pair of elongated hip support members are coupled side by side to the pelvis cushion support member, each of the elongated hip support member, of the pair of elongated hip support members having a second flexible material,
wherein the pair of elongated hip support members is aligned along the pelvis cushion support member at a height greater than a height of the pelvis cushion support member from the horizontal plane (H);
an inner layer coupled below the outer layer and extending across the pelvis cushion support member and at least partially across the pair of elongated hip support members; and
a liner layer coupled to the inner layer to support the inner layer and the outer layer;
a secondary elongated cushion member vertically extending from, and rotatably and detachably coupled to the primary elongated cushion member to support a spine region of the user: and
a headrest extension member detachably and adjustably coupled to the secondary elongated cushion member, the headrest extension member is configured to support a head of the user while the back body support is configured to the back of the user.

11. The back body support as claimed in claim 10, wherein the second flexible material of the pair of elongated hip support members is relatively softer than that of the first flexible material of the pelvis cushion support member, and wherein the inner layer having one or more blocks spaced from each other to support the pelvis cushion support member and the at least partially across the pair of elongated hip support members, wherein the one or more blocks are of a third flexible material having hardness greater than that of the first and second flexible materials, of the pelvis cushion support member and the pair of elongated hip support members.

12. The back body support as claimed in claim 10 wherein:
the secondary elongated cushion member comprises;
a vertical protrusion member rotatably and detachably coupled along a region of the pelvis cushion support member of the primary elongated cushion member,
an elliptical-shaped profile member snugly fits over the vertical protrusion member,
the elliptical-shaped profile member having at least one soft cushioning profile and at least one hard cushioning profile to be rotatably adjusted by a rotation of the vertical protrusion member along the region of the pelvis cushion support member of the primary elongated cushion member to provide support to the specific spine region depending upon a requirement of a hard support or a soft support to the specific spine region.

13. The back body support as claimed in claim 12, wherein the elliptical-shaped profile member having a length, and widths varying across the length, wherein the length of the elliptical-shaped profile member is configured to vary to be accommodated across an entire length of the vertical protrusion member, or across a partial length of the vertical protrusion member extending from a top to along a middle portion of the vertical protrusion member to provide support a specific spine region, and wherein the widths of the elliptical-shaped profile member is configured to vary across the entire length thereof to provide support to the specific spine region without restricting a movement of shoulder of the user.

14. The back body support as claimed in claim 10 further comprising:
a flexible seating support member detachably coupled to the pelvis cushion support member of the primary elongated cushion member,
wherein the flexible seating support member comprises a non-slip surface and is shaped to be accommodated on a conventional seat for supporting a buttock of the user while user is seating thereon.

15. The back body support as claimed in claim 14 further comprising:
a tail bone and buttocks support member detachably coupled to the flexible seating support member and to the pelvis cushion support member along an angular orientation between the flexible seating support member and to the pelvis cushion support member,
wherein the tail bone and buttocks support member comprises a stepped and curved configuration lying along the angular orientation between the flexible seating support member and to the pelvis cushion support member.

16. The back body support as claimed in claim 14 further comprising:
a rigid seat member to receive the flexible seating support member thereon, and to be detachably coupled thereto, the rigid seat member having,
a seating surface, and a back supporting surface extending from the seating surface, the pelvis cushion support member
wherein the flexible seating support member is received on the seating surface, and the pelvis cushion support member and the pair of elongated hip support members is supported over the back supporting surface.

17. The back body support as claimed in claim 10 further comprising:
- a posture correction member coupled to the primary elongated cushion member and the secondary elongated cushion member, the posture correction member having,
- a rigid frame structure, the rigid frame structure including,
- first and second horizontally aligned bar members, in a spaced relation, wherein the first horizontally aligned bar member is adapted to be aligned along a shoulder of the user and the second horizontally aligned bar member is adapted to be aligned the pelvis of the user, and wherein the first horizontally aligned bar member is longer than the second horizontally aligned bar member, and
- a third vertically aligned bar member coupled to and extending between and beyond first and second horizontally aligned bar members;
- a pair of shoulder straps, each shoulder strap of the pair of shoulder straps is coupled to opposite distal ends of the first horizontally aligned bar member such that both the ends of each shoulder strap are met at the respective opposite distal ends,
- a belt strap coupled to the second horizontally aligned bar member, the belt strap having buckles to be coupled and decoupled for closing and opening, and
- a coupling member including a hook-and-loop arrangement strip coupled to the third vertically aligned bar member of the rigid frame structure and across the belt strap to couple with the primary elongated cushion member and the secondary elongated cushion member, thereby coupling the primary elongated cushion member and the secondary elongated cushion member with the posture correction member.

18. A posture correction device comprising:
- a back body support having a primary elongated cushion member, and a secondary elongated cushion member; and
- a posture correction member having,
- a rigid frame structure, the rigid frame structure including,
- first and second horizontally aligned bar members, in a spaced relation, wherein the first horizontally aligned bar member is adapted to be aligned along a shoulder of the user and the second horizontally aligned bar member is adapted to be aligned the pelvis of the user, and wherein the first horizontally aligned bar member is longer than the second horizontally aligned bar member, and
- a third vertically aligned bar member coupled to and extending between and beyond first and second horizontally aligned bar members;
- a pair of shoulder straps, each shoulder strap of the pair of shoulder straps is coupled to opposite distal ends of the first horizontally aligned bar member such that both the ends of each shoulder strap are met at the respective opposite distal ends,
- a belt strap coupled to the second horizontally aligned bar member, the belt strap having buckles to be coupled and decoupled for closing and opening, and
- a coupling member including a hook-and-loop arrangement strip coupled to the third vertically aligned bar member of the rigid frame structure and across the belt strap to couple with the primary elongated cushion member and the secondary elongated cushion member, thereby coupling the primary elongated cushion member and the secondary elongated cushion member with the posture correction member.

19. The posture correction device as claimed in claim 18, wherein the back body support comprises:
- the primary elongated cushion member extending along a horizontal plane (H), the primary elongated cushion member having:
- an outer layer adapted to support pelvis and side hip regions of a user, the outer layer having,
- a pelvis cushion support member adapted to support the pelvis region of the user, wherein the pelvis cushion support member having a first flexible material, and
- a pair of elongated hip support members adapted to support the side hip regions of the user, each elongated hip support member, of the pair of elongated hip support members are coupled side by side to the pelvis cushion support member, each of the elongated hip support member, of the pair of elongated hip support members having a second flexible material,
- wherein the pair of elongated hip support members is aligned along the pelvis cushion support member at a height greater than a height of the pelvis cushion support member from the horizontal plane (H),
- an inner layer coupled below the outer layer and extending across the pelvis cushion support member and at least partially across the pair of elongated hip support members, and
- a liner layer coupled to the inner layer to support the inner layer and the outer layer; and
- the secondary elongated cushion member vertically extending from, and rotatably and detachably coupled to the primary elongated cushion member to support a spine region of the user, the secondary elongated cushion member having,
- a vertical protrusion member rotatably and detachably coupled along a region of the pelvis cushion support member of the primary elongated cushion member,
- an elliptical-shaped profile member snugly fits over the vertical protrusion member,
- the elliptical-shaped profile member having at least one soft cushioning profile and at least one hard cushioning profile to be rotatably adjusted by a rotation of the vertical protrusion member along the region of the pelvis cushion support member of the primary elongated cushion member to provide support to the specific spine region depending upon a requirement of a hard support or a soft support to the specific spine region.

\* \* \* \* \*